United States Patent [19]

Hedin et al.

[11] Patent Number: 4,922,907
[45] Date of Patent: May 8, 1990

[54] METHOD FOR FINDING THE PARAMETERS IN A FUNCTIONAL RELATIONSHIP BETWEEN STIMULATION FREQUENCY AND LOAD CONDITION SENSOR SIGNALS IN A RATE RESPONSIVE HEART PACEMAKER

[75] Inventors: Asa Hedin, Stklm, Lennart Moberg, Spanga; both of Sweden

[73] Assignee: Siemens Aktiengesellschaft, Berlin and Munich, Fed. Rep. of Germany

[21] Appl. No.: 205,333

[22] Filed: Jun. 10, 1988

[30] Foreign Application Priority Data

Jun. 17, 1987 [SE] Sweden .................. 87025235

[51] Int. Cl.$^5$ .............................................. A61N 1/00
[52] U.S. Cl. .............................. 128/419 P; 128/419 PG
[58] Field of Search ............ 128/419 P, 419 PG, 696, 128/700, 707; 364/413.01, 413.02

[56] References Cited

U.S. PATENT DOCUMENTS

| 4,428,378 | 1/1984 | Anderson et al. | 128/419 PG |
| 4,535,774 | 8/1985 | Olsen | 128/419 PG |
| 4,596,251 | 6/1986 | Plicchi et al. | 128/419 PG |
| 4,726,383 | 2/1988 | Cook et al. | 128/419 P |
| 4,730,619 | 3/1988 | Koning et al. | 128/419 P |
| 4,803,987 | 2/1989 | Calfee et al. | 128/419 P |

OTHER PUBLICATIONS

Wirtzfeld et al., "Regulation of Pacing Rate by Variations of Mixed Venous $O_2$ Saturation," 11-1984, PACE, vol. 7.

Primary Examiner—Lee S. Cohen
Assistant Examiner—Kennedy J. Schaetzle
Attorney, Agent, or Firm—Hill, Van Santen, Steadman & Simpson

[57] ABSTRACT

A method of finding rate responsive parameter settings in a functional relationship between sensor signal and stimulation frequency for a pacemaker by selecting desired heart rates optimal for a patient with respect to certain work loads. The respectively corresponding sensor signal values are obtained from the sensor, and the parameters are calculated by inserting the sensor signal values and selected frequencies into the functional relationship.

5 Claims, 1 Drawing Sheet

METHOD FOR FINDING THE PARAMETERS IN A FUNCTIONAL RELATIONSHIP BETWEEN STIMULATION FREQUENCY AND LOAD CONDITION SENSOR SIGNALS IN A RATE RESPONSIVE HEART PACEMAKER

BACKGROUND OF THE INVENTION

1. Field of the Invention

This invention relates to a method for finding the parameters in a functional relationship between the stimulation frequency in an implantable physiological stimulating device such as a heart pacemaker, and a sensor signal indicative of the physical load condition of a patient in whom the device is implanted.

2. Description of the Prior Art

Recently, pacemakers including a control system for matching the stimulation frequency of a heart pacemaker to the varying work load condition of a patient, generally referred to as rate responsive pacemakers, have been developed. Typically, rate responsive pacemakers rely on the sensing of a variable related to and indicative of the work load of a patient. Such variables are, for instance, blood oxygen saturation, blood pH, patient movement and force. The functional relationship between the sensed variable and the stimulation frequency could be linear or non-linear, depending on the sensed variable, the sensor type and the sensor signal processing.

Irrespective of the type of functional relationship, linear or non-linear as the case may be, the parameters in the function must be set to values which are optimal to the individual pacemaker patient, as the sensor output signals varies from patient to patient depending on general fitness, body constitution, pacemaker placement, etc.

In the prior art these technical parameters were directly set, as illustrated in an example of a prior art pacemaker disclosed in U.S. Pat. A-4,428,378. That known pacemaker has a sensor of the piezoelectric transducer type, and varies the stimulation frequency in response to sensed activity as a linear function with the slope as a programmable parameter. The slope parameter value is set by the physician and transmitted to the pacemaker by telemetry, to control pacemaker interaction with the patient.

However, directly setting the parameter values presents a problem to the physician because the mathematical character of these parameters, exemplified by slope in the type above, lack immediate or recognizable connection to the corresponding heart rate, which is the quantity familiar to the physician. Also, direct parameter value setting is inconvenient to the patient because an unexperienced physician must use a trial and error technique to find an optimal setting.

SUMMARY OF THE INVENTION

An object of the present invention is to provide a method in which the parameter values are found in response to desired stimulation frequency settings, and thus provide for a more fast, safe and convenient parameter setting.

Generally speaking, it is mathematically well known that any function between two variables can be determined when a sufficient number of variable values is known. Therefore, a function relating the sensor signal or measured variable m to stimulation frequency $f_{stim}$ could be determined with regard to its parameters from a number of observed values $f_{stim\ 1}$ to $f_{stim\ n}$ and $m_1$ to $m_n$ where n at least equals the number of parameters to be set. Thus, in principle, though time-consuming for a complex function, by observing $f_{stim}$ and m for a sufficient number of different work loads, parameter calculation is possible.

However, the inventors have observed that the typical relationship between the sensor signal m and the stimulation frequency $f_{stim}$ is or could be arranged to be a function of the linear or exponential (or logarithmic) type, viz. can be expressed as $f_{stim} = k_1 m + k_2$ or $f_{stim} = k_1 \exp(k_2 m)$ (or $f_{stim} = k_1 \log(k_2 m)$), where $k_1$ and $k_2$ are parameters to be determined.

Therefore, in practice, normally only two parameters must be determined, and consequently the variable values for only two workloads of the patient have to be observed.

It should be noted however, that although especially advantageous for the linear or exponential (logarithmic) relationship, the method is fully workable for more complex functions.

DESCRIPTION OF THE PREFERRED EMBODIMENTS

Figure 1:
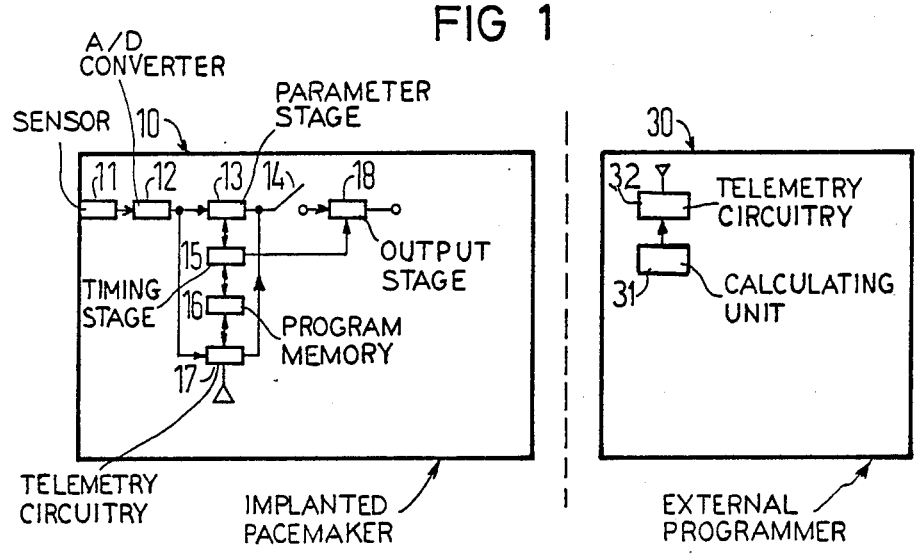
FIG. 1 is a functional block diagram of a rate-responsive pacemaker constructed in accordance with the principles of the present invention.

In FIG. 1 the pacemaker is generally designated 10. A force sensor 11 is included in the pacemaker housing. Other sensor types and also other sensor placements could be used. The sensor signal is transformed in an A/D-converter 12 into a signal m with a pulse duration proportional to the amplitude of the original sensor signal. Subsequently, the rate responsive parameters (calculated in the manner described below) defining the constants of the function relating the sensor signal to the stimulation frequency f are entered in a parameter stage 13. The parameter stage 13 is under the control of a logic and timing stage 15, also controlling other functions of the pacemaker (e.g. output stage 18), which, except for the rate responsive part, is a conventional demand pacemaker. When a switch 14 is closed the digital signals from the converter 12 cause a corresponding output from the parameter stage 13 to be supplied to the output stage 18. This output is a frequency signal based on the function (including the entered parameters) which has been selected to relate sensor signals to stimulation frequency. This output from stage 13 causes the output stage 18 to generate stimulation pulses at the correlated frequency.

Switch 14 also enables a passive mode for the rate responsive function. With the switch 14 open the pacemaker operates at the programmed minimum rate, while the rate which would have been present with switch 14 closed is still indicated from sensor 11.

The program memory 16 enables the programming signal and the calculated parameter values to be stored. The memory 16 may be, or include, a look-up table in which the parameters are entered. That signal contains the desired stimulation frequency and is received from the programmer 30 through telemetry circuitry 17 and 32. The parameter calculating unit 31 could either be contained in the timing stage 15 or the programmer 30 and is shown in the programmer 30 by way of example.

Figure 2:
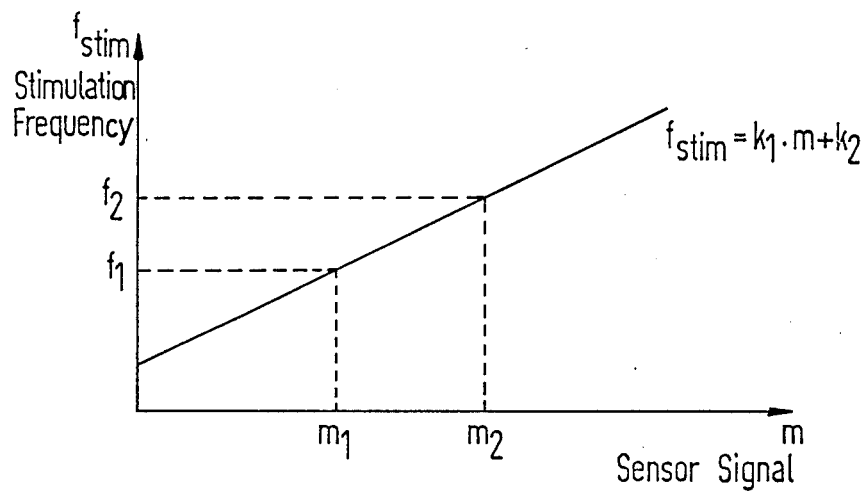
FIG. 2 is a graph illustrating the linear relationship between sensor signal and stimulation frequency for describing the method disclosed herein.

Setting of the rate responsive parameters is now described in connection with FIG. 2. In FIG. 2 a linear function ($f_{stim} = k_1 m + k_2$, with $k_1$ and $k_2$ representing slope and threshold respectively) between a sensor signal m and stimulation frequency is illustrated.

First, the patient is exposed to a low work load, for instance slow walking. This work load is correlated with a range of stimulation frequencies, e.g. 70–90 pulses per minute. The physician selects from this range one frequency $f_1$ appearing to be desirable to the individual pacemaker patient. The same level of work load corresponds to a sensor signal value $m_1$ indicative of this work load, which value is obtained from the pacemaker sensor 11.

Second, a repetition of the above steps is carried out for another work load, for instance fast walking. This work load is correlated with another range of stimulation frequencies, e.g. 130–150 and the physician again selects a desirable frequency, $f_2$. The corresponding sensor signal value is $m_2$.

The rate responsive parameters $k_1$ and $k_2$ can now be calculated either in the pacemaker circuitry or in the programmer by inserting $m_1$, $m_2$ and $f_1$, $f_2$ into the function. Thus, in accordance with the described method, slope and threshold are set in a way such that the physician is confronted only with choosing desired stimulation frequencies, as opposed to having to select possibly unfamiliar mathematical slope and threshold parameters.

In a non-linear relationship of the exponential or logarithmic type, where the function also includes two parameters, the same way of parameter setting applies, viz. for different work loads the values $m_1$, $m_2$ and $f_1$, $f_2$ are established and inserted into the function.

The invention has been described for a heart pacemaker just by way of example, and it should be noted that it applies to any implantable physiological stimulating device with a similar relationship between sensor signal and stimulation frequency.

Although modifications and changes may be suggested by those skilled in the art it is the intention of the inventor to embody within the patent warranted hereon all changes and modifications as reasonably and properly come within the scope of their contribution to the art.

We claim as our invention:

1. A method for finding the values of a number of parameters in a functional relationship between the stimulation frequency of a physiological stimulating device implanted in a patient and a sensor signal obtained from the patient indicative of a physical load condition of the patient, said method comprising the steps of:
   (a) subjecting the patient to a first physical load condition;
   (b) selecting a first stimulation frequency for optimally stimulating said patient under said first load condition;
   (c) obtaining a first sensor signal from said patient indicative of said first load condition;
   (d) repeating steps (a), (b) and (c) for at least one further load condition, the repetition resulting in at least one further stimulating frequency and at least one further sensor signal corresponding to said at least one further load condition, the total of said first load condition and said at least one further load condition being equal to the number of said parameters to be found; and
   (e) calculating said parameters in said functional relationship based on said stimulating frequencies and said sensor signals corresponding to all of said load conditions.

2. A method as claimed in claim 1, wherein step (e) is further defined by calculating said parameters based on a linear relationship between said stimulating frequencies and said sensor signals.

3. A method as claimed in claim 1, wherein step (e) is further defined by calculating said parameters based on a exponential relationship between said stimulating frequencies and said sensor signals.

4. A method as claimed in claim 1, wherein step (e) is further defined by calculating said parameters based on a logarithmic relationship between said stimulating frequencies and said sensor signals.

5. A method as claimed in claim 1 comprising the additional step of:
   (h) storing the parameters calculated in step (e) in a look-up table.

* * * * *